United States Patent

Cuschieri

[11] Patent Number: 5,836,936
[45] Date of Patent: Nov. 17, 1998

[54] DEVICE FOR PERFORMING ENDOSCOPIC OPERATIONS BY MEANS OF A SHEATH

[75] Inventor: Alfred Cuschieri, Dundee, Great Britain

[73] Assignee: Karl Storz GmbH & Co., Tuttlingen, Germany

[21] Appl. No.: 532,684
[22] PCT Filed: Feb. 7, 1995
[86] PCT No.: PCT/DE95/00157
  § 371 Date: Mar. 5, 1996
  § 102(e) Date: Mar. 5, 1996
[87] PCT Pub. No.: WO95/20915
  PCT Pub. Date: Aug. 10, 1995

[30] Foreign Application Priority Data

Feb. 7, 1994 [DE] Germany .......................... 44 03 567.5

[51] Int. Cl.⁶ .................................................. A61B 17/00
[52] U.S. Cl. ................................................. 606/1; 600/37
[58] Field of Search .......................... 600/37, 562; 606/1, 606/110, 113, 114, 127, 151, 213

[56] References Cited

U.S. PATENT DOCUMENTS 5,176,687  1/1993  Masson et al. .......................... 606/127
5,279,548  1/1994  Keine .
5,480,410  1/1996  Cuschieri ................................ 606/213

FOREIGN PATENT DOCUMENTS

| 0507588 | 10/1992 | European Pat. Off. . |
| 9212714 U | 12/1992 | Germany . |
| 4220785 | 1/1994 | Germany . |
| A9211816 | 7/1992 | WIPO . |
| 9214407 | 9/1992 | WIPO . |
| A9315671 | 8/1993 | WIPO . |
| A9315675 | 8/1993 | WIPO . |
| A9426179 | 11/1994 | WIPO . |

*Primary Examiner*—Glenn K. Dawson
*Attorney, Agent, or Firm*—Donald D. Mon

[57] ABSTRACT

A sheath for use in endoscopic surgery. A tubular proximal section fits in a trocar, along with a folded tubular distal section. The trocar inserts the distal section into a body cavity where it opens to receive severed tissue. A closure closes the distal end of the distal section to retain severed tissue. An abrupt transition section may join the proximal and distal sections. The material of the sheath is tough enough to enable external force to be applied to the tissue through the sheath without rupturing it. An optimal third tubular section may remain outside the body so tissue can be worked on outside of the body and returned into it.

3 Claims, 3 Drawing Sheets

DEVICE FOR PERFORMING ENDOSCOPIC OPERATIONS BY MEANS OF A SHEATH

SPECIFICATION

FIELD OF THE INVENTION

The present invention relates to a device for performing endoscopic operations, including a flexible sheath receiving detached parts.

BACKGROUND OF THE INVENTION

An endoscopic operation is frequently performed in order to detach and remove an endogenic sample. To this end the various cutting instruments have been proposed for detaching and removing endogenic samples, e.g. of tissue, organs or parts of organs, tumors, or calculi from the bladder, the gall bladder, the kidneys, or similar parts of the organism.

A serious problem is entrainment by these instruments which consists in the aspect that an infection of the surrounding regions of the body or of the surrounding healthy tissue along the duct through the tegument of the body as a result of the removal procedure cannot be definitely precluded. The risk of an infection occurs particularly when malignant ulcers are to be detached and removed.

This risk must be avoided on principle by the provision that upon termination of the detaching procedure, the sample to be taken is introduced into a container introduced into the body, that this container is closed and then removed out of the body, together with the detached sample, through passages either available or created for the operation.

From the European Patent EP 0 507 588 A1 an endoscopic instrument for medical applications has become known which comprises a bag adapted to be closed, which is disposed at the distal end of the instrument and which may be introduced into the body interior through a body orifice and, in open condition, permits the introduction of detached samples of the organism. This bag may be closed by operation of an operating mechanism provided on the proximal end. The closed bag may then be removed from the body interior, without running the risk of an infection of parts of the body as a result of dispersion of pathogenic germs and/or cancerous cells etc.

The document WO 92/14407 discloses an extraction bag for endoscopic surgery, which is mounted on an instrument adapted to be introduced into and removal in or from the body interior, and which is provided with an opening which may be closed again.

Moreover, the document WO 92/11816 describes a container which may be introduced into the body interior, either through natural or artificially established body orifice, and serves there as bag-shaped container for receiving tissue, organs or parts of organs, tumors, calculus-shaped deposits and sediments such as nephroliths, or other endogenic samples, which have been treated by various medical auxiliaries. In this case, too, a bag is involved which is provided with a single opening and which, as such, consists of a rigid material so that to a certain extent reducing operations may be performed on the objects introduced into the bag.

Finally, the German Patent DE 42 20 785 A1 discloses a laparoscopic bag having a funnel-shaped configuration, which provides for a collection of detached parts of the body inside a narrow funnel-shaped converging region. Like the afore-mentioned extraction bags, this design, too, has only a single opening.

Even though the known designs for extraction bags, which have been presented in the foregoing, have as an objective that samples detached inside the body, which possibly contain substances or cells which are harmful to the body, are removed from the interior of the body while the risk of an infection of the surrounding parts of the body due to dispersion of pathogenic germs, malignant cells, bacteria, etc. is avoided. And yet these known containers entail certain disadvantages:

Firstly, the intracorporeal charging of the proposed extraction bags is a complex operation: the known bags have, as a matter of fact, only a single opening into which the detached sample particles must be "scooped" by means of specific instruments. This procedure requires a certain space for unrestricted movement, which, however, is available inside the body, i.e. in a body cavity, in rare cases only.

When endogenic samples are taken by means of the aforementioned extraction bags the maximum size of the endogenic sample to be removed is, on principle, restricted by the dimensions of the body orifice through which the instruments are introduced together with the extraction bag. If samples are detached inside the body, whose size exceeds the size of the orifice, it is necessary to cut or crush them to a size in which they may be removed through the body orifice to the outside after they have been introduced into the bag. Even though it is possible that this cutting or crushing operation is performed already inside the extraction bag it cannot be precluded, even in a very diligently performed operation, that substances and materials which are harmful to the body and which may be released from the sample material during this operation of sample cutting and crushing will penetrate into the surrounding intracorporeal region since the known extraction bags are not provided with reliable provisions for closing the bag opening tightly against a crushing instrument inserted into the bag.

A contamination of the healthy surrounding tissue is therefore not precluded in this manner.

All the known extraction bags are designed for exclusive use as container units to be charged and closed inside the body. As a matter of fact, they do not offer any possibility of manipulating the detached samples inside the closed bag by means of suitable instruments.

BRIEF DESCRIPTION OF THE INVENTION

The present invention is therefore based on the problem of proposing a device for performing endoscopic operations inside an intracorporeal sheath, which precludes practically completely any potential intracorporeal infection caused by detached endogenic samples during the operations of detaching, cutting or crushing and removal from the body.

Moreover, the inventive device has been designed to offer the possibility of manipulating the sheath introduced into the interior of the body, e.g. by insufflation, in such a way that sufficient space for free movement in handling the samples inside the body may be created. In this respect the inventive sheath should equally offer an opportunity of simplifying the required set of surgical instruments so as to permit the handling of endogenic samples in intracorporeal regions, where pressures may be present which are different from the pressure conditions in the extracorporeal region, from the outside, as far as possible without any major inconvenience.

The invention is based on the idea of performing endoscopic operations inside an intracorporeal sheath having at least two openings.

The sheath presenting this inventive design is, as a general rule, introduced into the appropriate region of the body, e.g. into the abdomen, after the endogenic sample has been detached, e.g. from tissue or a part of an organ. The opening of the sheath, which presents a hose-shaped extension, protrudes through the introduction sleeve from the body. A manipulating instrument, which is introduced from the outside into the abdominal cavity, is passed through this sheath opening in such a way that the manipulating instrument draws the detached endogenic sample into the sheath directly, through the second wider opening through which the manipulating instruments protrudes.

The openings on the sheath may be so dimensioned that the smaller opening permits the passage, e.g. of a manipulating or gripping instrument, while the wider opening allows for the introduction of organs or parts of organs or similar detached parts. The latter opening part should be conveyed to the outside, preferably through a second punctured aperture, and then be closed by means of the appropriate specific ligating element. When the sheath element has been closed it is drawn again into the body whereupon the part of the tissue is processed appropriately. The smaller opening of the inventive sheath is preferably designed to fit so snugly against the introducer passed through the opening, or to be additionally linked up with the instrument or the introduction sleeve, by means of a ligating element, so tightly that any exchange of matter or substances between the interior of the sheath and the remaining intracorporeal space is precluded.

The sheath is preferably made of a ductile material and suitable for insufflation, i.e. inflation, by means of appropriate auxiliaries such as so-called insufflators. In this manner an enclosed space is created inside the body interior which permits the realization of further processing steps separately from the healthy environment in the body. For instance, the endogenic samples may be crushed in a controlled manner by means of cutting or crushing tools, under observation by means of endoscopes which possibly protrude into the sheath space, e.g. via the other sheath opening.

When the crushing operation has been finished the sheath may be completely removed, e.g. via the second opening and through the abdominal wall.

The inventive device for performing endoscopic operations in the intracorporeal region inside a sheath hence permits for the first time that endogenic sample or part of an organ, which has been detached for further examination and analysis, may be cut or crushed in a controlled manner inside the body by means of an additional cutting instrument such that they may be conveyed, on the one hand, to the outside together with the sheath through a body orifice, without excessively extending the narrow body orifice, and, on the other hand, that they may be composed again so as to re-establish their previous shape for a histologic analysis.

With the inventive device a medical tool has been created which may be used to create an enclosed space inside the body in which surgical operating steps, preferably endoscopic operations, may be performed.

Moreover, another inventive aspect provides for a configuration of the afore-described sheath in which the sheath is introduced into the intracorporeal region only partly, rather than in its entirety, so that the sheath forms an intracorporeal and an extracorporeal sheath portion while it passes through a body orifice—even of major extension. By means of this inventive embodiment it is possible to maintain the intracorporeal pressure conditions also inside the extracorporeal sheath portion, on the condition that the orifices provided in this region are tightly isolated from the outside atmosphere. If self-sealing openings are employed the manipulation with instruments which may be introduced into the sheath or direct manual operation can be substantially facilitated. In this way organs or parts of organs, which have been passed to the outside through the body orifice, for instance and which are still linked up with various other inner parts of the body, may be manipulated in any desired manner inside the extracorporeal sheath portion. The application of endoscopes, which permit only a narrow restricted field of vision despite the progresses in technology, may hence be dispensed with in the extracorporeal portion of the sheath.

BRIEF DESCRIPTION OF THE DRAWINGS

In the following the present invention will be described, by way of examples based on various embodiments, without any restriction of the global inventive idea, referring to the drawing which explicit reference is moreover made to in relation to the disclosure of all the inventive details which are not explained more exhaustively in the text. In the drawings.

Figure 1:
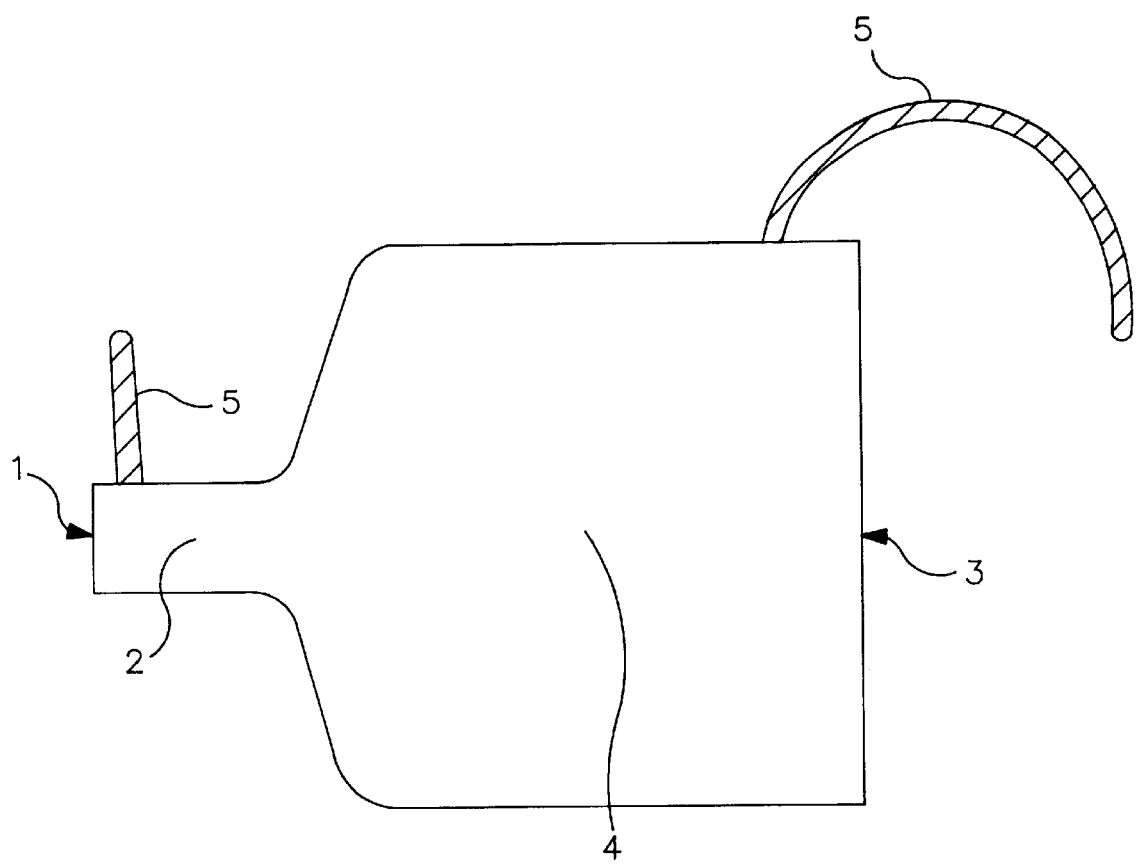
FIG. 1 is a cutaway side view of the preferred embodiment of the invention.

A particularly expedient embodiment of the inventive sheath is illustrated in FIG. 1. The sheath presents two openings, i.e. a small opening 1 and a wider opening 3. The size of the opening 1 as well as of the joining narrow straight opening duct 2 is intended to permit the passage of endoscopic instruments, preferably through an introducing sleeve. The opening duct 2 flares, relative to the total length of the inventive sheath, within a short region up to the diameter of the wider opening 3, cooperating with this larger diameter so as to form an equally straight sheath duct 4 which is longer than the opening duct 2.

The wider sheath opening 3 is so dimensioned that even organs or parts of organs of major size may pass therethrough and hence arrive in the interior of the sheath duct 4. The typical sheath diameter in the sheath duct 4 is 100 mm, approximately, at a duct length of some 500 mm.

Moreover, the inventive sheath presents ligating or elements or binders 5 on its two openings 1 and 3. These ligating elements 5 are preferably designed in the form of strip-shaped closing means adapted to be wound around the respective opening for tightly closing the openings 1 or 3, respectively, and sealing them from the outside of the sheath.

The sheath shape as such resembles a bottle shape which makes it possible to draw endogenic samples into the inside space of the sheathes for manipulation there. The often sharp-edged endoscopic instruments for cutting or crushing the detached samples must not violate the sheath wall. For this reason, the sheath is made of a tear-resistant material such as Nylon. Furthermore, the sheath material should be resilient, easy to sterilize and transparent so that it may be used without any problems in medical endoscopic applications while it permits potential insufflation.

FIGS. 2a to 2d show a succession of schematic views of the typical mode of application of the inventive sheath. The Figures represent a cross-section taken through the abdominal cavity inside which a part of an organ 6 to be detached is to be removed from the intracorporeal region. Two artificial apertures or orifices have been expediently created through the abdominal wall 7 for the introduction of the endoscopic instruments via two introducing shafts (trocar shafts) 8 into the cavity inside the body.

Figure 2A:
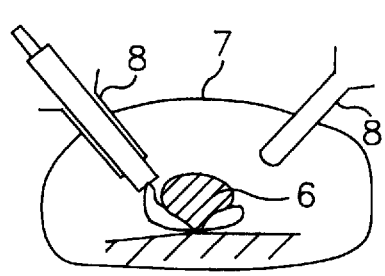
FIGS. 2a, 2b, 2c, and 2d are schematic cutaway side views showing sequential method steps according to this invention.

In FIG. 2a an endoscopic cutting instruments has been introduced through the left trocar shaft 8, which presents a cutter means on its distal end—in the Figure a cutter loop is illustrated—and which severs the part of an organ 6 to be detached from the remaining part of the organ.

Figure 2B:
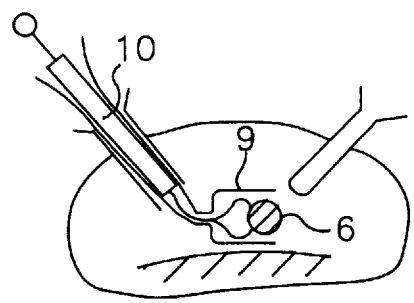

In a subsequent step, which is illustrated in FIG. 2b, the inventive sheath 9 is introduced into the interior of the body, which sheath is initially folded to a minimum size for potential introduction through one of the two passing shafts—the sheath is preferably introduced through the illustrated right trocar shaft since the set of instruments for fixing the detached part of the body has been introduced through the left shaft. After the folded sheath 9 has been placed into the body cavity it unfolds itself to its previously defined shape if the sheath material or parts thereof has shape-memory properties. On the other hand, the sheath may be unfolded and insufflated inside the body by means of appropriate endoscopic means. In the condition illustrated in FIG. 2b a manipulating or gripping instrument 10 is passed through the smaller opening on the sheath 9, under endoscopic observation, which instrument has a distal end for gripping the detached part of an organ 6 and draws it into the interior of the sheath 9 by appropriate operation. To this end the narrow sheath duct 2 is expediently drawn through that trocar shaft through which the manipulating instrument 10 protrudes. This provision avoids already a potential contamination with the surrounding tissue.

Figure 2C:
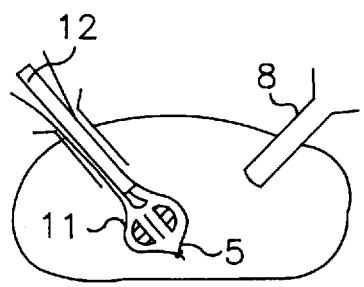

After the detached endogenic sample has been placed inside the sheath 9 the wider sheath opening must be tightly closed by means of the ligating element 5, using suitable means which may be introduced, for instance, through the left trocar shaft 8 into the intracorporeal cavity according to FIG. 2c. In this manner a separate sealed cavity is created inside the body, inside which the sample is to be crushed or cut by means of suitable cutting means 12 in such a way that the segments 11 of the sample may be composed with each other again upon removal from the body for a histological analysis.

The sheath volume may preferably be increased by the insufflation of the unilaterally tightly sealed sheath bag from the outside by means of a suitable supply instruments (not illustrated), e.g. with $CO_2$ gas, so as to facilitate the operation inside the bag. Owing to its shape, the inventive sheath ensures that the cutting element protrudes through the small opening on the sheath 9 and seals same from the outside of the intracorporeal body region. Thus another sealed cavity is created inside the body, from which no substances may escape which could infect the remaining parts of the body region. When the detached part of the organ has been suitably cut or crushed by means of the cutting instrument inside the enclosed sheath the cutting instrument is removed.

Figure 2D:
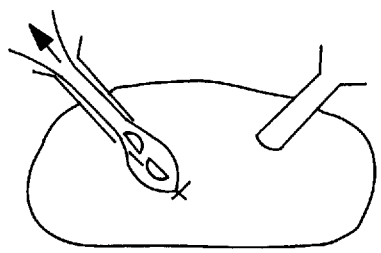

In accordance with FIG. 2d then the inventive sheath is withdrawn through the left trocar shaft 8 to the outside.

The inventive sheath offers a surgical auxiliary for a reliable and safe removal of endogenic samples, which is easy to operate while it does not incur any risk of contaminating healthy tissue by possibly malignant cells during the sampling and removal operations.

Figure 3:
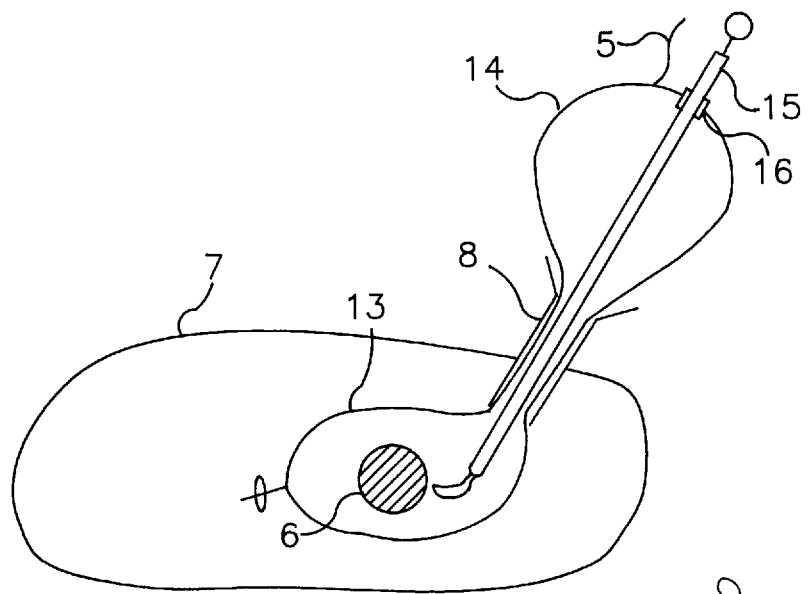
FIG. 3 is a cutaway side view showing another embodiment of the invention in a step in its use.
Figure 4:
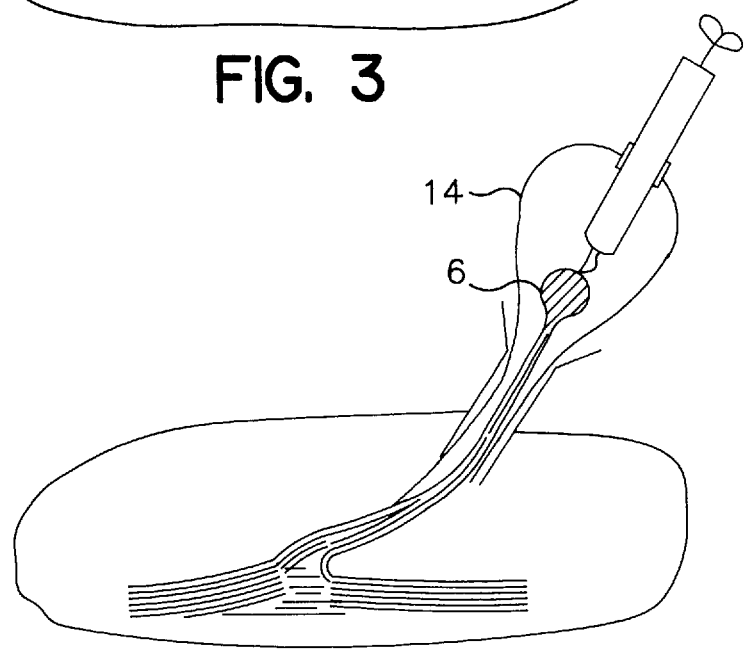
FIG. 4 is a cutaway side view showing the embodiment of FIG. 3 in a step in its use.

FIGS. 3 and 4 illustrate a slightly modified inventive sheath device which allows for a transmission of the intracorporeal pressure conditions to the outside within an external sheath. Both FIGS. 3 and 4 show a cross-section taken through an abdominal wall 7, with a passage duct 8 through which a sheath has been partly introduced into the interior of the body. FIGS. 3 and 4 show an intracorporeal sheath portion 13 and an extracorporeal sheath portion 14.

The intracorporeal sheath portion 13 contains, according to the upper part in FIG. 3, an endogenic sample 6 already detached, which has arrived in the interior cavity of the sheath by means of the aforedescribed operation. A cutting instrument 15, which protrudes through part of the extracorporeal sheath portion 14 into the intracorporeal sheath portion 13, permits the crushing of endogenic samples 6. This technique of operation is preferably applicable in those cases in which the locations operated on are situated in body regions where pressure conditions prevail which are different from the conditions in the extracorporeal region. A typical application is the placing of links for interconnecting intestinal segments, i.e. so-called anastomoses.

The opening 16 in the extracorporeal sheath portion 14 is so configured here that an exchange of matter or substances cannot take place between the introduced instrument 15 and the sheath wall. It is only in this way that one can ensure that the pressure conditions prevailing inside the entire sheath may be maintained constant. The sealing is either achieved by means of a ligating element 5 to be provided separately, or it is ensured by a self-sealing aperture.

FIG. 4 shows the case where part of an endogenic sample 6 to be processed has been conveyed into the extracorporeal sheath portion 14 inside which it is possible to perform the operation without any endoscopic viewing equipment, provided that the sheath material is transparent.

I claim:

1. A sheath for receiving and protectively enclosing tissue severed during an endoscopic procedure, said sheath being foldable for insertion into a body catheter through a trocar, said sheath comprising:

a tubular body formed of a flexible, fluid impermeable material having a tubular proximal section, a tubular distal section, and a tubular transition section connecting said proximal and distal sections, said distal section having a diameter substantially larger than the diameter of the proximal section, and the transition section enlarging abruptly from said proximal to said distal section, said proximal section being proportioned to fit in said trocar shaft without substantial folding, and said distal section being proportioned to receive tissue of substantial size;

closure means to close the distal end of said distal section to retain contents in said distal section; and a third tubular section which joins said proximal section, said third section having a diameter substantially larger than the diameter of the tubular proximal section, whereby, with said proximal section inside a said trocar and the distal section inside a cavity, said third section can receive tissue which is passed from said distal section through said proximal section, to enable procedures to be performed without exposing said tissue to the atmosphere, said third tubular section having an opening therethrough to permit the passage of an instrument into said third tubular section, and if desired also through said proximal and distal sections.

2. A sheath according to claim 1 in which said material is sufficiently strong and tough as to permit compressive forces to be exerted through said sheath on its contents without rupture of said material, whereby tissue inside said sheath can be reduced to bodies of lesser size from the outside of said sheath.

3. A sheath for receiving and protectively enclosing tissue severed during an endoscopic procedure, said sheath being foldable for insertion into a body catheter through a trocar, said sheath comprising:

a tubular body formed of a flexible, fluid impermeable material having a tubular proximal section, and a tubular distal section connected to one another, said distal section having a diameter substantially larger than the diameter of the proximal section, said proximal section being proportioned to fit in said trocar without substantial folding, and said distal section being proportioned to receive tissue of substantial size;

closure means to close the distal end of said distal section to contain contents in said distal section and a third tubular section which joins said proximal second, said third section having a diameter substantially larger than the diameter of the tubular proximal section, whereby, with said proximal section inside a said trocar and distal section inside a cavity, said third section can receive tissue which is passed from said distal section through said proximal section, to enable procedures to be performed without exposing said tissue to the atmosphere, said third tubular section having an opening therethrough to permit the passage of an instrument into said third tubular section, and if desired also through said proximal and distal sections.

* * * * *